(12) United States Patent
Mellul et al.

(10) Patent No.: US 6,432,417 B1
(45) Date of Patent: Aug. 13, 2002

(54) COSMETIC COMPOSITION CONTAINING SOLID ORGANIC PARTICLES COATED WITH A CATIONIC POLYMER

(75) Inventors: Myriam Mellul, L'Hay les Roses; Didier Candau, Melun, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 08/397,141

(22) PCT Filed: Sep. 13, 1993

(86) PCT No.: PCT/FR93/00878

§ 371 (c)(1),
(2), (4) Date: Apr. 21, 1995

(87) PCT Pub. No.: WO94/06406

PCT Pub. Date: Mar. 31, 1994

(30) Foreign Application Priority Data

Sep. 11, 1992 (FR) .............................................. 92 10885

(51) Int. Cl.[7] .............................................. A61K 7/218
(52) U.S. Cl. .......................... 424/401; 424/63; 424/64; 424/69; 424/70.1; 424/70.7; 424/78.02; 424/78.03; 424/78.08; 424/78.16; 424/78.37
(58) Field of Search .............................. 424/63, 64, 69, 424/400, 401, 70.1, 78.02, 78.03, 78.08, 78.16, 78.37; 514/844, 937, 938, 951

(56) References Cited

U.S. PATENT DOCUMENTS 4,492,686 A * 1/1985 Guillon et al. ................ 424/61

FOREIGN PATENT DOCUMENTS

| EP | 0209879 | 1/1987 |
| EP | 0212870 | 3/1987 |
| EP | 0220617 | 5/1987 |
| EP | 0445342 | 9/1991 |
| FR | 2234359 | 1/1975 |
| GB | 2107186 | 4/1983 |

* cited by examiner

*Primary Examiner*—Jyothsna Venkat
(74) *Attorney, Agent, or Firm*—Nixon & Vanderhye P.C.

(57) ABSTRACT

Cosmetic composition for the skin or skin appendages comprising a dispersion of solid organic particles in a binder and characterized in that at least a part of said organic particles is introduced in said composition in the form of particles having their surface coated with at least one cationic polymer. The cationic polymer comprises, for example, units containing primary, secondary, tertiary and/or quaternary amine groupings. The particles coated in this way are readily dispersible, even in fatty binders. The cosmetic compositions obtained show good adhesion to the skin and, in the case of compacted compositions, good cohesion properties.

14 Claims, No Drawings

COSMETIC COMPOSITION CONTAINING SOLID ORGANIC PARTICLES COATED WITH A CATIONIC POLYMER

This application is a 371 of PCT/FR93/00878 filed Sep. 13, 1993.

The subject of the present invention is cosmetic compositions, containing a dispersion of solid particles, into which are introduced solid organic particles whose surface is coated with a cationic polymer.

It is known that various make-up products such as loose or compacted powders, foundations, blushers, eye shadows, as well as lipsticks, are provided in the form of compositions comprising a dispersion of solid organic particles in a fatty binder. They may be anhydrous compositions or else oil-in-water or water-in-oil emulsions.

Depending on the types of compositions, the solid organic particles are especially pigments (white and/or coloured), intended to confer on the skin of the face or lips a certain colouring, or even to colour the compositions themselves, or alternatively particles which act as fillers (in particular in compositions in the form of powders).

In lipsticks, the solid particles dispersed in an appropriate fatty binder are especially coloured pigments, optionally in combination with white pigments (for example fine particles of titanium dioxide) which make it possible to impart a shade to the colours provided by the coloured pigments.

Such coloured pigments are also used in nail varnish compositions which essentially consist of a dispersion of these pigments in a solution of a film-forming polymer and of a plasticizer in an appropriate organic solvent.

The preparation and use of the cosmetic compositions containing dispersions of solid particles pose several types of problem. One problem common to the preparation of all the compositions which have just been discussed lies in the difficulty of obtaining stable dispersions, so as to apply, for example to the skin, a regular make-up whose application is uniform and which retains a good homogeneity. For this, specialists have been led to perform surface treatments on the powders used, especially in order to modify the interfacial properties involved in the wetting and dispersion phenomena. The aim of these treatments is often to render the powder hydrophobic in order to enhance its incorporation into the formulation binders and oils, and to increase the stability of the dispersion by reducing the phenomena of flocculation and aggregation; see for example European Patent 279,319 which describes the coating of pigments with siliconized polymers.

These treatments therefore make it possible to solve the problems of stability of the dispersion by limiting the flocculation phenomena. However, they do not solve another important problem, namely the weak properties of adhesion of the solid particles to the skin. Indeed, it is known that the solid particles used especially in the compositions in the form of powders have only weak properties of adhesion to the skin. The surface treatments intended to improve the stablity of the dispersions in the fatty binders do not provide a substantial improvement as far as the adhesion properties are concerned.

It is known furthermore that the make-up products for the face and for the eyes are often provided in the form of compacted powders. The compacted powders are prepared by mixing the constituents of the powder with a binding agent and then converted to the desired form by compression in appropriate containers.

The compacted powders should exhibit special characteristics of hardness. The hardness is a function of the applied compacting pressure. If the compacted product is too soft, it will be highly brittle and too large a quantity of product will be removed at the time of application. In contrast, if it is too hard, the disintegration will be difficult. Furthermore, a compact product should exhibit a perfectly flat surface. Finally, it should respond favourably to the drop test, that is to say exhibit a reduced loss of weight after a drop performed under standardized conditions.

It has now been discovered that it is possible to obtain cosmetic compositions, comprising a dispersion of solid organic pigments in a binder, having good properties of stability and adhesion to the skin or to superficial body growths, by introducing into the said compositions solid organic particles whose surface has been coated with a cationic polymer. It was observed, surprisingly, that the coating of the solid organic particles with cationic polymers, which nevertheless constitute a hydrophilic coating, does not prevent a good dispersibility of the particles in the fatty binders from being obtained. In addition, the compacted compositions obtained with cationic polymer-coated solid organic particles surprisingly exhibit good cohesion properties which result especially in a very satisfactory behaviour in the drop test. Furthermore, the compositions thus obtained have good properties of adhesion to the skin or to superficial body growths (fingernails or nails), after application.

The subject of the present invention is therefore a cosmetic composition for the skin or superficial body growths (fingernails or nails), comprising a dispersion of solid organic particles in a binder, characterized in that at least a portion of the said organic particles are introduced into the said composition in the form of particles whose surface is coated with at least one cationic polymer.

In the compositions of the invention, solid organic particles are coated with the cationic polymer at the surface. This means that, after coating, there is neither a change in morphology nor notable modification in the sizes of the particles, as verifiable by electron microscopy.

In the present application, the expression "cationic polymer" denotes a polymer containing cationic groups or groups which can be ionized to cationic groups.

The preferred cationic polymers are chosen from those containing units comprising primary, secondary, tertiary and/or quaternary amine groups which may either form part of the polymer chain or be carried by a side substituent.

The cationic polymers used preferably have a molecular mass of between $10^3$ and $3\times10^6$, approximately.

Preferably, the coated organic particles used in the compositions of the invention are coated solely with one (or more) cationic polymer(s).

The cationic polymers used are in particular those having a quaternization value, expressed as cationic equivalents per gram of polymer, of at least 0.05 cationic meq/g. Use is especially made of cationic polymers which contain for example at least 10% by weight of units comprising amine or quaternary ammonium groups.

When the cationic polymer contains amine or quaternary ammonium groups carried by a side substituent, the polymer chain is for example an acrylic, vinyl, siliconized, fluorinated or saccharide chain.

Among the cationic polymers, there may be mentioned more particularly quaternized proteins (or protein hydrolysates), quaternized polysiloxanes and polymers of quaternary polyammonium, polyaminoamide and polyamine type. These are known products.

Use is preferably made of cationic polymers which do not contain silicon, that is to say other than siliconized polymers.

It is more particularly preferable to use, as cationic polymer, a polymer containing ionized tertiary, secondary or primary amine group(s) or containing quaternary ammonium group(s), the latter being preferred.

The quaternary ammonium group may especially be obtained by quaternization of amino groups with conventional quaternization agents such as alkyl or aralkyl halides (for example methyl iodide, ethyl bromide or benzyl chloride), alkyl sulphates (for example dimethyl sulphate), and the like.

The ionized amine groups are obtained by salification of the amino groups with organic or inorganic acids such as hydrochloric, hydrobromic, lactic, acetic and glycolic acids and the like.

The quantities of polymer deposited on the particles vary with the procedure used for the coating. Generally, the proportion by weight of cationic polymer, relative to the total weight of the coated particles, is at least equal to 0.1%; the upper limit of the quantity of cationic polymer is sufficiently low for the particles to retain their individuality and their shape. In other words, the cationic polymer forms, at most, one thin (optionally lacunar) layer on the coated particles. Most often, the proportion by weight of cationic polymer in the coated particles is less than 10%, and in particular less than 8%, relative to the total weight of the coated particles.

The quaternized protein hydrolysates or proteins are in particular chemically modified polypeptides carrying at the chain end, or grafted thereto, quaternary ammonium groups. Their molecular mass can vary for example from 1500 to 10,000 and in particular from 2000 to 5000, approximately. Among these compounds, there may be mentioned especially:

hydrolysates of collagen carrying triethylammonium groups such as the products sold under the name "Quat-Pro E" by the Company Maybrook and termed in the CTFA dictionary "Triethonium Hydrolyzed Collagen Ethosulfate";

hydrolysates of collagen carrying trimethylammonium or trimethylstearylammonium chloride groups, sold under the name "Quat-Pro S" by the Company Maybrook and termed in the CTFA dictionary "Steartrimonium Hydrolyzed Collagen";

hydrolysates of animal proteins carrying trimethylbenzylammonium groups such as the products sold under the name "Crotein BTA" by the Company Croda and termed in the CTFA dictionary "Benzyltrimonium hydrolyzed animal protein";

hydrolysates of proteins carrying on the polypeptide chain quaternary ammonium groups comprising at least one alkyl radical having 1 to 18 carbon atoms.

Among these protein hydrolysates, there may be mentioned inter alia:

"Croquat L" whose quaternary ammonium groups comprise a $C_{12}$ alkyl group;

"Croquat M" whose quaternary ammonium groups comprise $C_{10}$–$C_{18}$ alkyl groups;

"Croquat S" whose quaternary ammonium groups comprise a $C_{18}$ alkyl group;

"Crotein Q" whose quaternary ammonium groups comprise at least one alkyl group having 1 to 18 carbon atoms.

These different products are sold by the Company Croda.

Other quaternized hydrolysates or proteins are for example those corresponding to the formula:

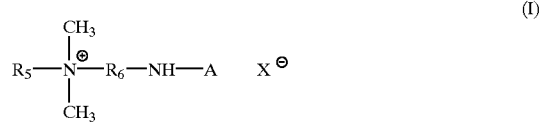

(I)

in which $X^-$ is an anion of an organic or inorganic acid, A denotes a protein residue derived from hydrolysates of collagen protein, $R_5$ denotes a lipophilic group comprising up to 30 carbon atoms and $R_6$ represents an alkylene group having 1 to 6 carbon atoms. There may be mentioned for example the products sold by the Company Inolex, under the name "Lexein QX 3000", termed in the CTFA dictionary "Cocotrimonium Collagen Hydrolysate".

There may also be mentioned quaternized plant proteins, such as wheat, maize or soya bean proteins: as quaternized wheat proteins, there may be mentioned those marketed by the Company Croda under the names "Hydrotriticum WQ or QM", termed in the CTFA dictionary "Cocodimonium Hydrolysed wheat protein", "Hydrotriticum QL", termed in the CTFA dictionary "Laurdimonium hydrolysed wheat protein", or alternatively "Hydrotriticum QS", termed in the CTFA dictionary "Steardimonium hydrolysed wheat protein".

Another family of cationic polymers is that of the siliconized cationic polymers. Among these polymers, there may be mentioned:

(a) the quaternized polysiloxanes termed in the CTFA dictionary "Amodimethicone" and corresponding to the formula:

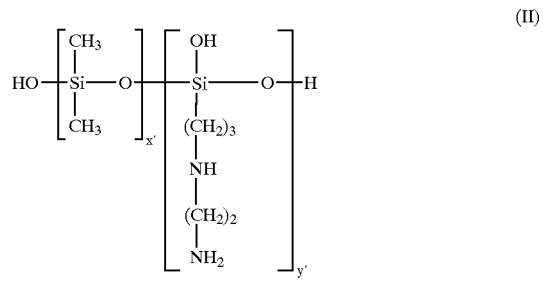

(II)

in which x' and y' are integers depending on the molecular weight, generally such that said molecular weight is between 5000 and 10,000, approximately;

(b) the siliconized cationic polymers corresponding to the formula:

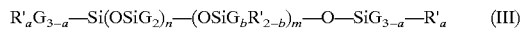

(III)

in which:

G is a hydrogen atom or a phenyl, OH or $C_1$–$C_8$ alkyl, for example methyl, group, a denotes the number 0 or an integer from 1 to 3, in particular 0, b denotes 0 or 1 and in particular 1, m and n are numbers such that the sum (n+m) can vary especially from 1 to 2000 and in particular from 50 to 150, it being possible for n to denote a number from 0 to 1999 and especially from 49 to 149 and it being possible for m to denote a number from 1 to 2000 and especially from 1 to 10;

R' is a monovalent radical of formula —$C_qH_{2q}L$ in which q is a number from 2 to 8 and L is an optionally quaternized amino group chosen for example from the groups:

—NR"—CH$_2$—CH$_2$—N'(R")$_2$
—N(R")$_2$
—N$^\oplus$(R")$_3$A$^\ominus$
—N$^\oplus$(R")H$_2$A$^\ominus$
—N(R")—CH$_2$—CH$_2$—N$^\oplus$R"H$_2$A$^\ominus$, in which R" may denote hydrogen, phenyl, benzyl or a monovalent saturated hydrocarbon radical, for example an alkyl radical having from 1 to 20 carbon atoms and A$^\ominus$ represents a halide ion such as for example fluoride, chloride, bromide or iodide.

A product corresponding to this definition is the polymer termed "trimethylsilylamodimethicone" corresponding to the formula:

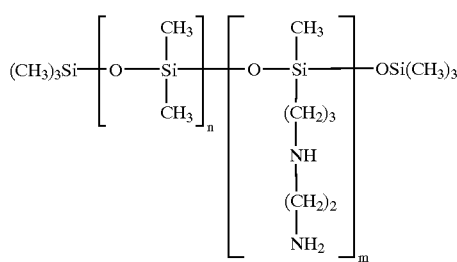

(IV)

in which n and m have the meanings given above (cf. formula III).

Such polymers are described for example in Patent Application EP-A-95238.

(c) the siliconized cationic polymers corresponding to the formula:

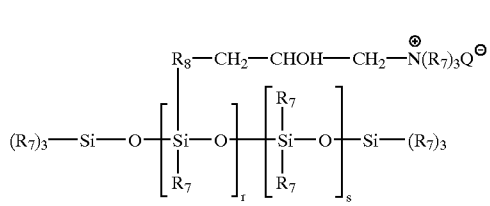

(V)

in which
R$_7$ represents a monovalent hydrocarbon radical having from 1 to 18 carbon atoms and in particular a C$_1$–C$_{18}$ alkyl or C$_2$–C$_{18}$ alkenyl, for example methyl, radical;
R$_8$ denotes a divalent hydrocarbon radical, especially a C$_1$–C$_8$ alkylene radical or a C$_1$–C$_{18}$, for example C$_1$–C$_8$ divalent alkylenoxy radical;
Q$^-$ is a halide, especially chloride, ion;
r represents a mean statistical value from 2 to 20 and in particular from 2 to 8;
s represents a mean statistical value from 20 to 200 and in particular from 20 to 50.

Such polymers are described more particularly in U.S. Pat. No. 4,185,087.

A polymer entering into this class is the polymer sold by the Company Union Carbide under the name "Ucar Silicone ALE 56".

When these siliconized polymers are used, a particularly advantageous embodiment is their simultaneous use with cationic and/or non-ionic surface-active agents. There may be used for example the product sold under the name "Emulsion Cationique DC 929" by the Company Dow Corning which comprises, in addition to amodimethicone, a cationic surface-active agent comprising a mixture of products corresponding to the formula:

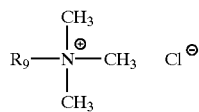

in which R$_9$ denotes alkenyl and/or alkyl radicals having from 14 to 22 carbon atoms, derived from tallow fatty acids, in combination with a non-ionic surface-active agent of formula:

C$_9$H$_{19}$—C$_6$H$_4$—(OC$_2$H$_4$)$_{10}$—OH known under the name "Nonoxynol 10".

Another commercial product which can be used according to the invention is the product sold under the name "Dow Corning Q2 7224" by the Company Dow Corning comprising in combination the trimethylsilylamodimethicone of formula (IV), a non-ionic surface-active agent of formula:

C$_8$H$_{17}$—C$_6$H$_4$—(OCH$_2$CH$_2$)$_n$—OH where n=40 also termed octoxynol-40, another non-ionic surface-active agent of formula:

C$_{12}$H$_{25}$—(OCH$_2$—CH$_2$)$_n$—OH where n=6 also termed isolaureth-6,
and glycol.

The polymers of quaternary polyammonium, polyamineoamide and polyamine type which can be used in conformity with the present invention may be those mentioned especially in French Patents Nos. 2,505,348 or 2,542,997. Among these polymers, there may be mentioned:

(1) the quaternized or non-quaternized dialkylaminoalkyl acrylate- or methacrylate-vinylpyrrolidone copolymers such as the products sold under the name "Gafquat" by the Company GAF Corporation such as for example Gafquat 734, 755 or HS100 or alternatively the product termed "Copolymer 937". These polymers are described in detail in French Patents 2,077,143 and 2,393,573.

(2) The cellulose ether derivatives comprising quaternary ammonium groups described in French Patent 1,492,597 and in particular the polymers marketed under the names "JR" (JR 400, JR 125, JR 30M) or "LR" (LR 400, LR 30M) by the Company Union Carbide Corporation. These polymers are also defined in the CTFA dictionary as quaternary ammonium salts of hydroxyethyl cellulose having reacted with an epoxide substituted by a trimethylammonium group.

(3) The cationic cellulose derivatives such as the cellulose copolymers or cellulose derivatives grafted with a water-soluble quaternary ammonium monomer and which are described especially in U.S. Pat. No. 4,131,576, such as hydroxyalkyl celluloses, like hydroxymethyl, hydroxyethyl or hydroxypropyl celluloses grafted especially with a salt of methacryloylethyltrimethylammonium, methacrylamidopropyltrimethylammonium or dimethyldiallylammonium.

The commercial products corresponding to this definition are more particularly the products solds under the name "Celquat L 200" and "Celquat H 100" by the Company National Starch.

(4) The cationic polysaccharides described more particularly in U.S. Pat. Nos. 3,589,578 and 4,031,307 and more particularly the product marketed under the name "Jaguar C. 13 S" sold by the Company Meyhall.

(5) The polymers consisting of piperazinyl units and straight- or branched-chain divalent alkylene or hydroxyalkylene radicals, optionally interrupted by one or more oxygen, sulphur or nitrogen atoms and/or by aromatic or heterocyclic rings as well as the oxidation and/or quaternization products of these polymers. Such polymers are described especially in French Patents 2,162,025 and 2,280,361.

(6) The water-soluble polyaminopolyamides prepared in particular by polycondensation of an acidic compound with a polyamine. These polyaminopolyamides may be crosslinked by an epihalohydrin, a diepoxide, a dianhydride, an unsaturated anhydride, a bis-unsaturated derivative, a bis-halohydrin, a bis-azetidinium, a bis-haloacyldiamine, an alkyl bis-halide or alternatively by an oligomer resulting from the reaction of a bifunctional compound reactive towards a bis-halohydrin, a bis-azetidinium, a bis-haloacyldiamine, an alkyl bis-halide, an epihalohydrin, a diepoxide or a bis-unsaturated derivative; the crosslinking agent being used especially in proportions ranging from 0.025 to 0.35 mol per amine group of the polyaminopolyamide.

These polyaminopolyamides may be alkylated or, if they comprise one or more tertiary amine functional groups, quaternized.

Such polymers are described in particular in French Patents 2,252,840 and 2,368,508.

(7) The polyaminopolyamide derivatives resulting from the condensation of polyalkylenepolyamines with polycarboxylic acids followed by an alkylation using bifunctional agents. There may be mentioned for example the adipic acid-dialkylaminohydroxyalkyl-dialkylenetriamine polymers in which the alkyl radical comprises 1 to 4 carbon atoms and especially denotes methyl, ethyl or propyl. Such polymers are described in French Patent 1,583,363.

Among these derivatives, there may be mentioned more particularly adipic acid-dimethylaminohydroxypropyl-diethylenetriamine polymers sold under the names "Cartaretine F, $F_4$ or $F_8$" by the Company Sandoz.

(8) The polymers obtained by reaction of a polyalkylenepolyamine comprising two primary amine groups and at least one secondary amine group with a dicarboxylic acid chosen for example from diglycolic acid, and saturated aliphatic dicarboxylic acids having 3 to 8 carbon atoms, the molar ratio of the polyalkylenepolyamine to the dicarboxylic acid being for example between 0.8:1 and 1.4:1, and the resulting polyaminopolyamide then being reacted with epichlorohydrin in a molar ratio of epichlorohydrin to the secondary amine groups of the polyaminopolyamide of between 0.5:1 and 1.8:1. Such polymers are described in particular in U.S. Pat. Nos. 3,227,615 and 2,961,347.

Polymers of this type are in particular marketed under the name "Hercosett 57" by the Company Hercules Incorporated or alternatively under the name "PD 170" or "Delsette 101" by the Company Hercules.

(9) The cyclopolymers such as homopolymers comprising as principal constituents of the chain units corresponding to the formulae (VI) or (VI')

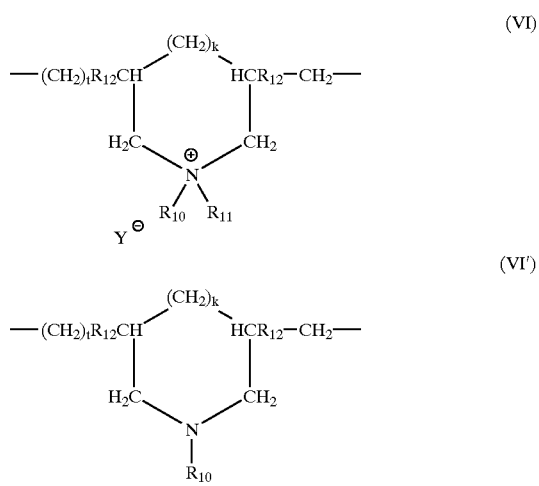

in which k and t are equal to 0 or 1, and the sum k+t=1, $R_{12}$ denotes hydrogen or methyl, $R_{10}$ and $R_{11}$ independently denote an alkyl group having from 1 to 22 carbon atoms, a hydroxyalkyl group in which the alkyl group especially has 1 to 5 carbon atoms, a lower amidoalkyl group in which the alkyl has especially 1 to 6C, and where $R_{10}$ and $R_{11}$ may denote together with the nitrogen atom to which they are attached heterocyclic groups such as piperidyl or morpholinyl, as well as the copolymers comprising both units of formulae (VI) or (VI') and units derived from acrylamide or diacetone acrylamide, $Y^{\ominus}$ is an anion such as bromide, chloride, acetate, borate, citrate, tartrate, bisulphate, bisulphite, sulphate, phosphate and the like. Among the polymers defined above, there may be mentioned more particularly the dimethyldiallylammonium chloride homopolymer sold under the name Merquat 100 and the dimethyldiallylammonium chloride and acrylamide copolymer sold under the name Merquat 550 by the Company Merck.

These polymers are described more particularly in French Patent 2,080,759 and its certificate of addition No. 2,190,406.

(10) The quaternary polyammonium polymer containing repeat units corresponding to the formula:

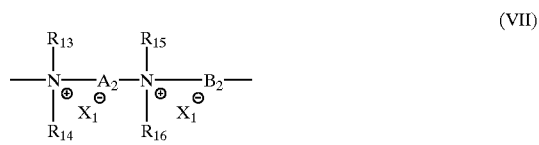

in which $R_{13}$ $R_{14}$, $R_{15}$ and $R_{16}$, being identical or different, represent aliphatic, alicyclic or arylaliphatic hydrocarbon radicals containing from 1 to 20 carbon atoms or lower hydroxyalkylaliphatic radicals, or alternatively the $R_{13}$ and $R_{14}$ and/or $R_{15}$ and $R_{16}$ pairs constitute, with the nitrogen atoms to which they are attached, heterocycles optionally containing a second heteroatom other than nitrogen or alternatively $R_{13}$, $R_{14}$, $R_{15}$ and $R_{16}$ represent a linear or branched $C_2-C_{16}$ alkyl radical substituted by a nitrile, ester, acyl or amide group or by a group

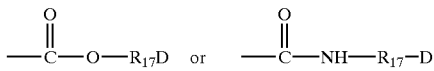

where $R_{17}$ is an alkylene and D a quaternary ammonium group, $A_2$ and $B_2$ represent alkylene, especially polymethylene, groups containing from 2 to 20 carbon atoms which may be linear or branched, saturated or unsaturated and which may contain, bonded to or intercalated into the principal chain, one or more aromatic rings, or one or more oxygen or sulphur atoms, or one or more SO, $SO_2$, disulphide, amino, alkylamino, hydroxyl, quaternary ammonium, ureido, amide or ester groups and $X_1^\ominus$ denotes an anion derived from an inorganic or organic acid, it being possible for $A_2$, $R_{13}$ and $R_{15}$ additionally to form, together with the two nitrogen atoms to which they are attached, a piperazine ring; in addition, when $A_2$ denotes a saturated or unsaturated, linear or branched alkylene or hydroxyalkylene radical, $B_2$ may also denote a group:

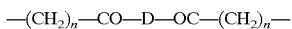

which D denotes:
a) a glycol residue of formula: —O—Z—O— where Z denotes a linear or branched hydrocarbon radical or a group corresponding to the formula:

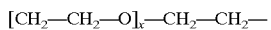

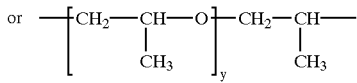

where x and y denote a number from 1 to 4 representing a mean or defined degree of polymerization;
b) a bis-secondary diamine residue such as a piperazine residue:

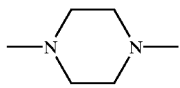

c) a bis-primary diamine residue of formula:

—NH—Y—NY— where Y denotes a linear or branched bivalent hydrocarbon radical or alternatively the radical

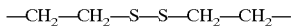

d) a ureylene group of formula:

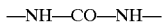

$X^\ominus$ is an anion such as chloride or bromide.

Polymers of this type are described in particular in French Patents 2,320,330, 2,270,846, 2,316,271, 2,336,434 and 2,413,907 and U.S. Pat. Nos. 2,273,780, 3,206,462, 2,375, 853, 2,388,614, 2,454,547, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) The quaternary polyammonium polymers consisting of units of formula:

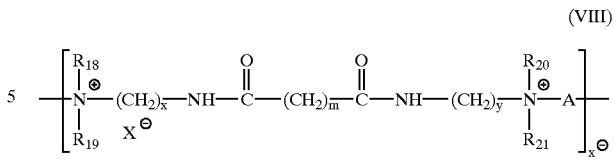

in which $R_{18}$, $R_{19}$, $R_{20}$ and $R_{21}$, which are identical or different, represent a hydrogen atom or a methyl, ethyl, propyl, β-hydroxyethyl, β-hydroxypropyl or —$CH_2CH_2$($OCH_2CH_2$)$_p$OH radical where p is the number 0 or an integer between 1 and 6, provided that $R_{18}$, $R_{19}$, $R_{20}$ and $R_{21}$ do not simultaneously represent a hydrogen atom, x and y, which are identical or different, are integers between 1 and 6;

m is the number 0 or an integer between 1 and 34,

X denotes a halogen atom,

A denotes the residue of a divalent hydrocarbon radical optionally comprising heteroatoms, and in particular the radical:

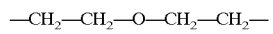

Such compounds are described especially in European Patent Application 122,324.

(12) The homopolymers or copolymers derived from acrylic or methacrylic acids and comprising units:

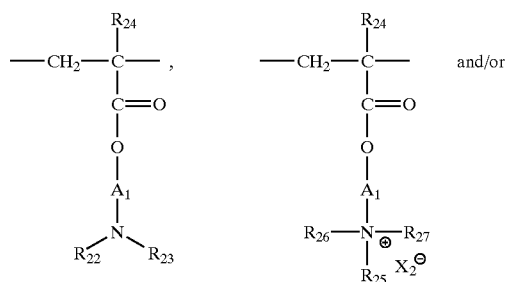

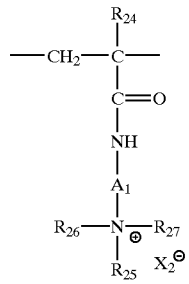

in which the $R_{24}$ groups independently denote H or $CH_3$, the $A_1$ groups independently denote a linear or branched alkyl group of 1 to 6 carbon atoms, or a hydroxyalkyl group of 1 to 4 carbon atoms, the $R_{25}$, $R_{26}$ and $R_{27}$ groups, which are identical or different, independently denoting an alkyl group having from 1 to 18 carbon atoms or a benzyl radical, $R_{22}$ and $R_{23}$ represent hydrogen or an alkyl group having from 1 to 6 carbon atoms, $X_2^-$ denotes an anion, for example methosulphate or halide such as chloride or bromide.

The comonomer(s) which can be used in the preparation of the corresponding copolymers belongs (belong) to the family of the acrylamides, methacrylamides, diacetone acrylamides, acrylamides and methacrylamides which are nitrogen-substituted by lower alkyls, alkyl esters of acrylic or methacrylic acids, vinylpyrrolidone or vinyl esters.

(13) The quaternary vinylpyrrolidone and vinyl imidazole polymers such as for example the products marketed under the names Luviquat FC 905, FC 550 and FC 370 by the Company B.A.S.F.

Other cationic polymers which can be used in conformity with the invention are polyalkyleneimines, in particular polyethyleneimines, polymers containing vinylpyridine or vinylpyridinium units, condensates of polyamines and epichlorohydrin, quaternary polyureylenes and chitin derivatives.

Among the cationic polymers which can be used in the compositions of the invention, there may be mentioned especially the following polymers:

the polymer comprising units of formula:

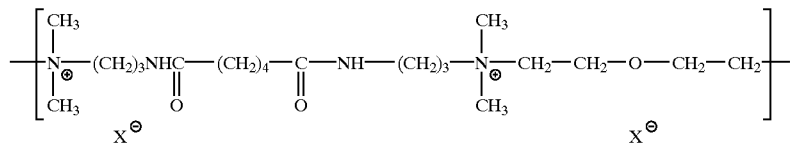

sold under the name "Mirapol AD 1". by the Company Miranol, the polymer comprising units of formula:

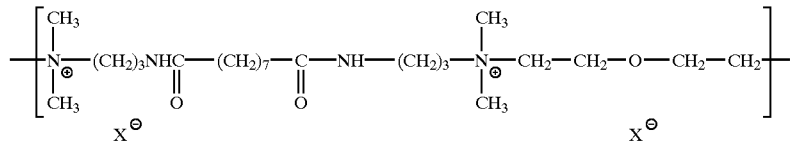

sold under the name "Mirapol AZ1" by the Company Miranol, poly(methacrylamidopropyltrimethylammonium chloride) sold under the name "Polymaptac" by the Company Texaco Chemicals;

the quaternized polymers of ionene type described in French Patent No. 2,270,846 and more particularly those comprising the units:

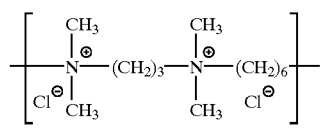

the quaternary ammonium polymers of the type described in U.S. Pat. No. 4,157,388 and more particularly that sold under the name "Mirapol A 15" by the Company Miranol;

poly(dimethylbutenylammonium chloride)-α,ω-bis (triethanolammonium chloride) sold under the name "Onamer M" by the Company Onyx Internationale.

The organic particles intended to be coated in conformity with the invention may optionally be particles having undergone beforehand one or more known surface treatments of chemical, electronic and/or mechanical nature. They may additionally be inorganic or organic particles coated with an organic substance, such as the composite particles which are described below.

The organic particles intended to be coated with a cationic polymer according to the invention comprise, for example:

cochineal carmine, carbon black, organic lakes or insoluble sodium, potassium, calcium, barium, aluminium, zirconium or strontium salts of acid dyes such as haloacid dyes, azo dyes, anthraquinone dyes, and the like. There may in particular be mentioned, among these lakes, those known under the following names:

| D & C Red No. | 2 | Aluminium lake |
| --- | --- | --- |
| D & C Red No. | 3 | Aluminium lake |
| D & C Red No. | 4 | Aluminium lake |
| D & C Red No. | 6 | Aluminium lake |
| D & C Red No. | 6 | Barium lake |
| D & C Red No. | 6 | Barium/strontium lake |
| D & C Red No. | 6 | Strontium lake |
| D & C Red No. | 6 | Potassium lake |
| D & C Red No. | 7 | Aluminium lake |
| D & C Red No. | 7 | Barium lake |
| D & C Red No. | 7 | Calcium lake |
| D & C Red No. | 7 | Calcium/strontium lake |
| D & C Red No. | 7 | Zirconium lake |
| D & C Red No. | 8 | Sodium lake |
| D & C Red No. | 9 | Aluminium lake |
| D & C Red No. | 9 | Barium lake |
| D & C Red No. | 9 | Barium/strontium lake |
| D & C Red No. | 9 | Zirconium lake |
| D & C Red No. | 10 | Sodium lake |
| D & C Red No. | 19 | Aluminium lake |
| D & C Red No. | 19 | Barium lake |
| D & C Red No. | 19 | Zirconium lake |
| D & C Red No. | 21 | Aluminium lake |
| D & C Red No. | 21 | Zirconium lake |
| D & C Red No. | 27 | Aluminium lake |
| D & C Red No. | 27 | Barium lake |
| D & C Red No. | 27 | Calcium lake |
| D & C Red No. | 27 | Zirconium lake |

-continued

| | | |
|---|---|---|
| D & C Red No. | 30 | Lake |
| D & C Red No. | 31 | Calcium lake |
| D & C Red No. | 33 | Aluminium lake |
| D & C Red No. | 34 | Calcium lake |
| D & C Red No. | 36 | Lake |
| D & C Red No. | 40 | Aluminium lake |
| D & C Blue No. | 1 | Aluminium lake |
| D & C Green No. | 3 | Aluminium lake |
| D & C Orange No. | 4 | Aluminium lake |
| D & C Orange No. | 5 | Aluminium lake |
| D & C Orange No. | 5 | Zirconium lake |
| D & C Orange No. | 10 | Aluminium lake |
| D & C Orange No. | 17 | Barium lake |
| D & C Yellow No. | 5 | Aluminium lake |
| D & C Yellow No. | 5 | Zirconium lake |
| D & C Yellow No. | 6 | Aluminium lake |
| D & C Yellow No. | 7 | Zirconium lake |
| D & C Yellow No. | 10 | Aluminium lake | melanin pigments derived from natural or synthetic sources and which can be obtained: (A) by oxidation of at least one indole compound, or (B) by oxidative or enzymatic polymerization of melanin precursors, or (C) by extraction of melanin from substances containing it, or (D) by culturing microorganisms.

(A) Melanin pigments can, in the first place, be obtained by oxidation of at least one indole compound chosen especially from those corresponding to the formula:

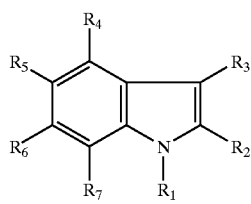

(IX)

in which:
R$_1$ and R$_3$ represent, independently of one another, a hydrogen atom or a C$_1$–C$_4$ alkyl group;
R$_2$ represents a hydrogen atom, a C$_1$–C$_4$ alkyl group, a carboxyl group or a (C$_1$–C$_4$)alkoxycarbonyl group;
the R$_4$ to R$_7$ substituents represent a hydrogen atom, a C$_1$–C$_4$ alkyl group or an —NHR° or —OZ group, R° denoting a hydrogen atom or a C$_2$–C$_4$ acyl or C$_2$–C$_4$ hydroxyalkyl group, and the Z radical denoting a hydrogen atom, a C$_2$–C$_{14}$ acyl group, a C$_1$–C$_4$ alkyl group or a trimethylsilyl group,
being understood that R$_5$ can additionally represent a halogen atom, and being understood that:
at least one of the R$_4$ to R$_7$ radicals represents an OZ or NHR° group, one at most of the R$_4$ to R$_7$ radicals representing NHR° and two at most of the R$_4$ to R$_7$ radicals representing OZ and, in the case where Z represents a hydrogen atom, the two OH groups are in the 5- and 6-positions; and at least one of the R$_4$ to R$_7$ radicals represents a hydrogen atom, and in the case where only one of these radicals represents a hydrogen atom, only one radical from the R$_4$ to R$_7$ radicals then represents NHR° or OZ, the other radicals representing a C$_1$–C$_4$ alkyl group or alternatively, if appropriate, for R$_5$, a halogen atom;
and their alkali metal, alkaline-earth metal, ammonium or amine salts, as well as the hydrochlorides, hydrobromides, sulphates and methanesulphonates.

The indole compounds of formula (IX) above are preferably chosen from 4-hydroxyindole, 5-hydroxyindole, 6-hydroxyindole, 7-hydroxyindole, 4-hydroxy-5-methoxyindole, 4-hydroxy-5-ethoxyindole, 2-carboxy-5-hydroxyindole, 5-hydroxy-6-methoxyindole, 6-hydroxy-7-methoxyindole, 5-methoxy-6-hydroxyindole, 5,6-dihydroxyindole, N-methyl-5,6-dihydroxyindole, 2-methyl-5,6-dihydroxyindole, 3-methyl-5,6-dihydroxyindole, 2,3-dimethyl-5,6-dihydroxyindole, 2-carboxy-5,6-dihydroxyindole, 4-hydroxy-5-methylindole, 2-carboxy-6-hydroxyindole, 6-hydroxy-N-methylindole, 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy-2,3-dimethylindole, 6-hydroxy-2-(ethoxycarbonyl)indole, 7-(β-hydroxy)-3-methylindole, 5-hydroxy-6-methoxy-2,3-dimethylindole, 5-hydroxy-3-methylindole, 5-acetoxy-6-hydroxyindole, 5-hydroxy-2-(ethoxycarbonyl)indole, 6-hydroxy-2-carboxy-5-methylindole, 6-hydroxy-2-ethoxycarbonyl-5-methoxyindole, 6-(N-β-hydroxyethylamino)indole, 4-aminoindole, 5-aminoindole, 6-aminoindole, 7-aminoindole, N-methyl-6-(hydroxyethylamino)indole, 6-amino-2,3-dimethylindole, 6-amino-2,3,4,5-tetramethylindole, 6-amino-2,3,4-trimethylindole, 6-amino-2,3,5-trimethylindole, 6-amino-2,3,6-trimethylindole, 5,6-diacetoxyindole, 5-methoxy-6-acetoxyindole, 5,6-dimethoxyindole, 5,6-methylenedioxyindole, 5,6-trimethylsilyloxyindole, the phosphoric ester of 5,6-dihydroxyindole, 5,6-dibenzyloxyindole and the addition salts of these compounds.

5,6-Dihydroxyindole is one of the preferred compounds.

Oxidation of the indole compound of formula (IX) can be carried out in aqueous or water/solvent(s) medium, exposed to the air, in the presence or absence of an alkaline agent and/or of a metal oxidation catalyst such as, for example, the cupric ion.

The reaction medium preferably consists of water and can, if appropriate, consist of a mixture of water and at least one solvent chosen so that it quickly dissolves the indole compound of formula (IX). Mention may be made among these solvents, by way of examples, of lower C$_1$–C$_4$ alcohols, such as ethyl alcohol, propyl or isopropyl alcohol or tert-butyl alcohol, alkylene glycols, such as ethylene glycol or propylene glycol, alkyl ethers of alkylene glycols, such as the monomethyl, monoethyl and monobutyl ethers of ethylene glycol or the monomethyl ethers of propylene glycol and of dipropylene glycol, and methyl lactate.

Oxidation can be also carried out by using hydrogen peroxide in the presence of an alkaline agent, such as preferably aqueous ammonia, or in the presence of an iodide ion, the iodide preferably being the iodide of an alkali metal or alkaline-earth metal or ammonium iodide.

It is also possible to carry out the oxidation by using periodic acid and its water-soluble salts and derivatives, permanganates and dichromates, for example of sodium or of potassium, sodium hypochlorite, potassium ferricyanide, ammonium persulphate, silver oxide, lead oxide, ferric chloride, sodium nitrite, the salts of rare-earth metals, including especially cerium, and organic oxidizing agents chosen from ortho- and para-benzoquinones, mono- or diimines of ortho- and para-benzoquinones, 1,2- and 1,4-naphthoquinones or mono- or dimines of 1,2- and 1,4-naphthoquinones, such as defined in Application EP-A-0, 376,776. The preferred salt of periodic acid is sodium periodate.

It is possible to activate the oxidizing agents with a pH modifier.

It is also possible to carry out an enzymatic oxidation.

The insoluble product is isolated by filtration, centrifuging, lyophilization or atomization; it is then ground or micronized in order to achieve the desired particle size.

(B) Melanin pigments can also arise from the oxidative or enzymatic polymerization of melanin precursors, such as L-tyrosine, L-dopa, catechol and their derivatives.

(C) Melanin pigments can finally arise on the extraction of melanin from natural substances such as human hair or cephalopod ink (cuttlefish, octopuses), alternatively known under the name of sepiomelanin, in which case the pigment is ground and purified before it is used.

(D) Melanin pigments can be obtained by culturing microorganisms. These microorganisms produce melanin either naturally or by genetic modification or by mutagenesis. Methods of preparation of these melanins are described, for example, in Patent Application WO-90 04029.

The melanin pigment can be present at the surface or incorporated in a coloured or uncoloured, lamellar or non-lamellar, inorganic or organic, particulate filler. Composite melanin pigments are thus obtained.

In this case, the melanin pigment can result from the oxidation of at least one indole compound of formula (IX), as defined above, as a mixture with the particulate filler, in a medium which is essentially non-solvent for the said filler, at a temperature which can range from room temperature to approximately 100° C., or alternatively can result from the oxidative polymerization of melanin precursor on the filler.

The non-lamellar inorganic particles used in this process are in particular inert inorganic particles having a particle size of less than 20 micrometers. Such particles are especially calcium carbonate, silica or titanium oxide particles.

Such composite melanin pigments, deposited on inorganic fillers, are described, as well as their preparation, in Patent Application FR-2,618,069.

By an analogous process, it is possible to prepare composite melanin pigments with coloured inorganic particles.

The appellation "coloured inorganic particles" is given to non-white particles consisting of metal salts, which are insoluble in the cosmetic medium, which can be used in cosmetics, such as those referenced in the Color Index under the chapter "Inorganic Colouring Matters" and carrying the numbers 77000 to 77947, with the exception of white pigments and particles which are provided in the lamellar form, such as lamellar iron oxide. These coloured inorganic particles can consist of a single pigment or of a mixture of pigments and can thus be provided in the form of nacreous or interferential pigments.

The coloured inorganic particles are in particular non-white particles, preferably chosen from iron oxides, with the exception of lamellar iron oxide, ultramarine blue (which is a complex sulphosilicate), chromium oxides, manganese violet (which is an ammonium manganese pyrophosphate) and Prussian blue (which is an iron ferricyanide).

Such composite melanin pigments, deposited on a coloured inorganic filler, are described in French Patent Application 92 0415, filed Jan. 16, 1992.

Lamellar particles are inorganic or organic particles which are provided in the form of optionally laminated layers. These layers are characterized by a thickness which is lower than the greater dimension of the particle. The ratio of the greater dimension to the thickness is preferably between 2 and 100. The greatest dimension is generally less than 50 micrometers. Such composite melanin pigments deposited on a lamellar filler are described, as well as their preparation, in European Patent Application No. 467,767.

The non-lamellar organic particles are particles of inert polymers chosen from crystalline or amorphous, organic or inorganic, natural or synthetic polymers with a crosslinked network having, for example, a molecular weight of between 5,000 and 5,000,000. Composite-melanin pigments on a polymeric filler, as well as their preparation, are described in European Patent Application No. 379,409;

the particles obtained by oxidative polymerization have at least one indoline compound of formula:

(X)

in which formula:

$R_{10}$ and $R_8$ represent, independently of one another, a hydrogen atom or a $C_1$–$C_4$ alkyl radical;

$R_9$ represents a hydrogen atom, a $C_1$–$C_4$ alkyl radical or a carboxyl or ($C_1$–$C_4$)alkoxycarbonyl group;

$R_{12}$ denotes a hydrogen atom, a $C_1$–$C_4$ alkyl, hydroxyl, alkoxy ($C_1$–$C_4$), amino or $C_1$–$C_{10}$ alkylamino radical or halogen;

$R_{11}$ denotes a hydrogen atom or a hydroxyl, $C_1$–$C_4$ alkoxy or amino group; with the condition that at least one of the $R_{11}$ or $R_{12}$ radicals denotes a hydroxyl, alkoxy or amino group; and with the condition that, when $R_{11}$ denotes an amino group, $R_{12}$ cannot denote an alkylamino radical;

it also being possible for $R_{11}$ and $R_{12}$ to form a $C_1$–$C_2$ alkylenedioxy group, when they are in the 5- and 6-positions;

and their salts.

The compounds corresponding to the formula (X) are chosen especially from the group consisting of 5,6-dihydroxyindoline, 6-hydroxyindoline, 5,6-methylenedioxyindoline, 7-methoxy-6-hydroxyindoline, 6,7-dihydroxyindoline, 5-hydroxy-4-methoxyindoline, 4,5-dihydroxyindoline, 5-methoxy-6-hydroxyindoline, 4-hydroxy-5-methoxyindoline, 5-hydroxy-6-methoxyindoline, 4,7-dihydroxyindoline, 6-aminoindoline, N-ethyl-4-hydroxyindoline, 1-ethyl-6-aminoindoline, 5,6-diaminoindoline, 1-methyl-6-aminoindoline, 2-methyl-6-aminoindoline, 3-methyl-6-aminoindoline, 2-methyl-5,6-diaminoindoline, 5-chloro-7-aminoindoline, 3-methyl-5,7-diaminoindoline, 5,7-diaminoindoline, 2-methyl-5,7-diaminoindoline, 7-aminoindoline, 2-methyl-7-aminoindoline, 4-aminoindoline, 4-amino-6-chloroindoline, 4-amino-6-iodoindoline, 4-amino-5-bromoindoline, 4-amino-5-hydroxyindoline, 4-amino-7-hydroxyindoline, 4-amino-5-methoxyindoline, 4-amino-7-methoxyindoline, 5-aminoindoline, 2,3-dimethyl-5-aminoindoline, 1-methyl-5-aminoindoline, 2-methyl-5-aminoindoline, 5-[N-(1-methylhexyl)amino]indoline, 5,6-dimethoxyindoline and 5,6-dihydroxy-2-carboxyindoline.

In the compounds of formula (X), the $C_1$–$C_4$ alkyl radicals preferably denote methyl, ethyl, propyl, isopropyl, butyl or isobutyl; the $C_1$–$C_{10}$ radicals preferably denote methyl, ethyl, propyl, isopropyl, butyl, isobutyl, 1-methylhexyl, 1-methylheptyl or 1-methyloctyl; the alkoxy radicals preferably denote methoxy, ethoxy, propoxy and butoxy; halogen preferably denotes bromine, chlorine or iodine.

The salts of the compounds of formula (X) are, in particular, hydrochlorides, hydrobromides, sulphates or methanesulphonates or salts of alkali metals or alkaline-earth metals, of ammonium or of amines.

The particles obtained by co-oxidation of at least one indoline compound of formula (X) and of at least one indole derivative. The latter can be chosen from mono- and dihydroxyindoles or amino indoles, as described more particularly in Patent EP-A-2,398,826 and Patent Applications EP-A-425,345 and GB-A-2,224,754.

These indoles correspond more particularly to the formula (IX). During the co-oxidation, it is possible to use up to 50%, in moles, of indole derivatives with respect to the total number of moles of derivatives to be oxidized. The oxidation conditions are identical to those of the melanin pigments described above.

Just like the melanin pigments, the products resulting from the oxidative polymerization of at least one indoline compound of formula (X) may be present at the surface of a particulate filler or incorporated in the said coloured or uncoloured, lamellar or non-lamellar, inorganic or organic, particulate filler. These are then composite pigments.

The inorganic particulate fillers are those mentioned above for the composite melanin pigments.

The non-lamellar organic fillers are chosen from the particles of:
a) optionally modified polymers derived from keratin;
b) silk fibroins;
c) optionally deacetylated polymers derived from chitin;
d) cellulose polymers;
e) synthetic polymers chosen from:
  (i) optionally crosslinked poly(methyl methacrylate), polystyrene, polypropylene or polyethylene;
  (ii) crosslinked poly-β-alanine;
  (iii) crosslinked polymers of styrene-divinylbenzene, methyl methacrylate-ethylene glycol dimethacrylate or vinyl stearate-divinylbenzene;
  (iv) hollow microspheres of copolymers of vinylidene chloride and acrylonitrile;
  (v) porous microspheres of polyamide 12, polyamide 6 or copolyamide 6/12;
  (vi) silicone powders consisting especially of organosiloxane elastomers, resins or gums.

Such non-lamellar organic fillers are mentioned especially in European Patent Application No. 379,409.

The lamellar fillers are chosen from L-lauroyllysine, ceramic microparticles optionally covered with zirconium powder, lamellar titanium dioxide, lamellar talc, boron nitride, lamellar mica, bismuth oxychloride or transparent red iron oxide.

Such lamellar fillers are mentioned especially in European Patent Application No. 467,767.

Such composite pigments, as well as their preparation, are described especially in French Patent Application No. 92-00417, filed on Jan. 16, 1992.

In the compositions of the invention, the proportions of coated organic particles dispersed in the binder depend on the type of composition; the proportions are customary for the type of composition considered.

In order to coat the particles, a known method, for example one of the following methods, may be used:

1) A solution of the polymer is prepared in one of its good solvents. The powder to be coated is dispersed in this solution with vigorous stirring and a poor solvent for the polymer is added without proceeding up to the precipitation of the polymer in the solution, but only up to the first cloudiness. The suspension is then left vigorously stirring, for example for 4 hours. The suspension is allowed to settle, is rinsed with a non-solvent of the polymer and dried, for example at 80° C., under reduced pressure.

2) A solution of the polymer is prepared in which the powder to be coated is dispersed. The system is left vigorously stirring and a precipitant of the polymer is slowly added so as to gently precipitate the polymer at the surface of the powder. The mixture is allowed to settle, it is rinsed with a non-solvent of the polymer and the powder is dried.

3) A solution is prepared with a good solvent of the polymer and the powder to be coated is dispersed therein. A poor solvent of the polymer is chosen whose boiling point is greater than that of the good solvent and a slow evaporation of the system is carried out. This results in the formation of a coacervate which gradually coats the powder, and then the powder is dried.

4) The so-called fluidized air bed technique is used: a dilute solution of the polymer is sprayed hot in a cyclone in which the powder is kept buoyant.

5) A solution of the polymer is prepared in which the powder to be coated is dispersed. The system is left vigorously stirring and the solvent is evaporated slowly so as to gently precipitate the polymer at the surface of the powder. It is allowed to settle, rinsed with a non-solvent of the polymer and the powder is dried.

6) The technique of coating by atomization is used. A suspension of particles in water is prepared; once the suspension is homogenized, an aqueous solution of the polymer is introduced therein. The mixture is left stirring for 2 hours and the suspension is atomized in an atomizing device.

During the atomization, the mixture preferably remains under magnetic stirring.

7) The technique of coating by freeze-drying is used. The polymer is dissolved in water and then an aqueous suspension of particles is incorporated therein, with stirring. The mixture is left stirring for 6 to 8 hours and is then placed on the freeze dryer for at least 18 hours. A pulverulent product is recovered which is sieved.

The compositions of the invention may be anhydrous compositions. The anhydrous compositions are provided especially in the form of a compacted powder, a cast powder, a lipstick or a nail varnish.

The compositions of the invention may also be provided in the form of water-in-oil or oil-in-water type emulsions and may be used as foundation or mascara for example.

These compositions are prepared according to the customary methods.

In the make-up compositions, the binder is a customary fatty binder consisting of an oil, a mixture of oils or a mixture of oil and wax(es).

In the lipsticks, the binder is also a fatty binder generally consisting of a mixture of (natural or synthetic) waxes of high melting point, (synthetic, mineral or vegetable) oils and (natural or synthetic) waxes of low melting point.

In the nail varnishes, the binder consists of the solution of the film-forming polymer and the plasticizer in the chosen organic solvent.

In the emulsions, the binder is a customary fatty binder consisting of an oil or a mixture of oils.

When the composition comprises a micronized pigment of metal oxides chosen especially from titanium, zinc, cerium or zirconium oxides or mixtures thereof, it may constitute a composition for protecting the skin or hair against ultraviolet rays.

The invention also relates to the use, in the preparation of a cosmetic composition containing a dispersion of solid particles in a binder, of organic particles whose surface is coated with at least one cationic polymer. In this use, the composition, and especially the organic particles, the cationic polymer, as well as the binder, are in particular as defined above.

The following examples illustrate the invention without however limiting it.

EXAMPLE 1

6.74 g of melanin pigment (obtained by oxidative polymerization of 5,6-dihydroxyindole, in the presence of hydrogen peroxide in ammoniacal medium) and 0.675 g (active material) of a copolymer of vinylpyrrolidone and dimethylaminoethyl methacrylate quaternized with dimethyl sulphate, containing 50% by weight of vinylpyrrolidone units ("Gafquat HS 100" of the Company GAF sold as a 20% solution of active material) are mixed in 200 ml of water. Stirring is carried out for 6 hours.

The mixture is frozen in liquid nitrogen and then dried by freeze drying.

A black pigment coated with 2% of polymer (% by weight with respect to the melanin pigment) is obtained.

EXAMPLE 2

10 g of D & C Red No. 7 Calcium Lake organic pigment and 0.9 g (active material) of quaternized wheat protein ("Hydrotricum WQ" of the Company Croda, sold as a 28% solution of active material) are mixed in 500 ml of water and stirring is carried out for 3 hours. 130 ml of acetone are added. After 3 hours of contact, the pigment is recovered by centrifuging, rinsed, centrifuged again and then dried.

A pigment coated with 2.5% of polymer (weight % with respect to the pigment) is obtained.

Compositions Examples

| EXAMPLE A: Mascara | |
|---|---|
| PHASE A | |
| Stearic acid | 8.0 g |
| Glyceryl stearate | 2.0 g |
| Beeswax | 7.0 g |
| Carnauba wax | 2.55 g |
| Paraffin | 10.2 g |
| Propylparaben | 0.1 g |
| Coated melanin pigment | 1.5 g |
| PHASE B | |
| Hydroxyethyl cellulose sold under the name "Cellosize OP 4400 M" by the Company Amerchol | 0.5 g |
| Methylparaben | 0.3 g |
| Water | 63.95 g |
| PHASE C | |
| Triethanolamine | 3.9 g |

The coated melanin pigment used is that described in Example 1.

Procedure

Phase A is melted at 80–90° C.

Phase C is mixed with a portion of the water of the formula and added while hot to Phase A with vigorous stirring.

Gel B is prepared while hot (70° C.) and then added to (A+C).

The mascara is cooled to 25° C.

A mascara of smooth and homogeneous appearance is obtained, which adheres well to the eyelashes.

| EXAMPLE B: Lip gloss | |
|---|---|
| Lanolin | 23.6 g |
| Lanolin wax | 2.2 g |
| Liquid paraffin | 9.30 g |
| Microcrystalline wax | 17.70 g |
| Beeswax | 4.20 g |
| Butylhydroxytoluene | 0.15 g |
| Octylglyceryl behenate | 9.20 g |
| Sesame oil | 12.80 g |
| Oleic acid | 5.10 g |
| Titanium dioxide | 0.25 g |
| Coated pigment of Example 2 | 1.00 g |
| Castor oil | q.s. for 100.00 g |

The oils and the waxes constituting the fatty phase are melted at 90° C. The pigments are added. The mixture is ground and then reheated to 90° C. The ground mixture is poured into moulds.

| EXAMPLE C: Cream blusher | |
|---|---|
| PHASE A | |
| Liquid paraffin | 46.7 g |
| Petroleum jelly | 10.0 g |
| Carnauba wax | 5.0 g |
| Polyethylene wax | 5.0 g |
| Preserving agent | 0.2 g |
| PHASE B | |
| Iron oxides | 4.3 g |
| Titanium oxide | 8.4 g |
| Coated pigment of Example 2 | 0.4 g |
| PHASE C | |
| Nylon powder sold under the name "Orgasol" by the Company Atochem | 10.0 g |
| Titanium mica | 10.0 g |

Procedure

Phase A is melted at a temperature of 90–95° C.

Phase B is added thereto. The mixture may be ground for better dispersion of the pigments.

Phase C is added last until a homogeneous paste is obtained and the composition is then cooled to room temperature.

What is claimed is:

1. A cosmetic composition for the skin or nails, comprising a dispersion of solid organic particles in a binder, wherein at least a portion of the organic particles are introduced into the composition in the form of particles whose surface is coated with at least one cationic polymer.

2. The composition according to claim 1, wherein the cationic polymer contains at least one of primary, secondary, tertiary or quaternary amine groups.

3. The composition according to claim 2, wherein the amine group forms part of the polymer chain.

4. The composition according to claim 2, wherein the amine groups are carried by a side substituent.

5. The composition according to claim 1 wherein the cationic polymer has a quaternization value, expressed as cationic equivalents per gram of polymer, of at least 0.05 cationic meq/g.

6. The composition according to claim 1 wherein the cationic polymer contains at least 10% by weight of units comprising amine or quaternary ammonium groups.

7. The composition according to claim 1 wherein the proportion by weight of cationic polymers, relative to the total weight of the coated particles, is at least equal to 0.1%.

8. The composition according to claim 7, wherein the proportion is less than 10%.

9. The composition according to claim 7, wherein the proportion is less than 8%.

10. The composition according to claim 1 wherein the binder is selected from the group consisting of fats and film-forming polymers.

11. The composition according to claim 10 wherein said fats are at least one of oils or waxes.

12. The composition according to claim 1, in the form of a compacted powder, a cast powder, a lipstick or a nail varnish.

13. The composition according to claim 1, in the form of a water-in-oil emulsion or oil-in-water emulsion.

14. A cosmetic treatment method comprising applying to the skin or nails a cosmetic composition for the skin or nails comprising a dispersion of solid organic particles in a binder wherein at least a portion of the composition is in the form of particles whose surface is coated with at least one cationic polymer.

* * * * *